US 6,866,641 B2

(12) United States Patent
Marshall

(10) Patent No.: US 6,866,641 B2
(45) Date of Patent: Mar. 15, 2005

(54) SKIN PRICKERS

(75) Inventor: Jeremy Marshall, Oxford (GB)

(73) Assignee: Owen Mumford Limited, Oxford (GB)

(*) Notice: Subject to any disclaimer, the term of this patent is extended or adjusted under 35 U.S.C. 154(b) by 121 days.

(21) Appl. No.: 10/182,376

(22) PCT Filed: Nov. 26, 2001

(86) PCT No.: PCT/GB01/05181
§ 371 (c)(1),
(2), (4) Date: Nov. 15, 2002

(87) PCT Pub. No.: WO02/43591
PCT Pub. Date: Jun. 6, 2002

(65) Prior Publication Data
US 2003/0130597 A1 Jul. 10, 2003

(30) Foreign Application Priority Data
Nov. 28, 2000 (GB) ............................................ 00289264

(51) Int. Cl.⁷ ................................................ A61B 5/00
(52) U.S. Cl. ........................ 600/583; 600/573; 606/181
(58) Field of Search ................................. 600/573, 583, 600/584; 606/181–185; 604/192, 197, 198

(56) References Cited
U.S. PATENT DOCUMENTS

| 5,439,473 A | 8/1995 | Jorgensen |
| 5,487,748 A | 1/1996 | Marshall et al. |
| 5,554,166 A | 9/1996 | Lange et al. |
| 5,707,384 A | 1/1998 | Kim |
| 5,741,288 A | 4/1998 | Rife |
| 5,913,868 A * | 6/1999 | Marshall et al. ............. 606/181 |
| 6,136,013 A | 10/2000 | Marshall et al. |
| 6,156,051 A * | 12/2000 | Schraga ...................... 606/181 |
| 6,168,606 B1 * | 1/2001 | Levin et al. ................. 606/181 |
| 6,258,112 B1 | 7/2001 | Schraga |
| 6,261,264 B1 * | 7/2001 | Tamaro ....................... 604/198 |

FOREIGN PATENT DOCUMENTS

DE 197 18 081 11/1998

* cited by examiner

Primary Examiner—Charles Marmor
(74) Attorney, Agent, or Firm—Young & Thompson

(57) ABSTRACT

A skin pricker for blood sampling has a barrel housing a lancet which can be pushed back against a spring to a primed condition, by an elongate cap over its needle tip there to be held by a trigger. The cap (4) is removed by twist and pull action. The lancet body has integrally formed spring arms extending rearwardly and alongside, and when the lancet is fired these are momentarily flexed inwardly as their tips snap past abutments within the barrel. These act as ratchets, providing a first defence against re-priming of the pricker. If that first defence is overcome by a substantial rearward force on the lancet, the spring arms rearward pointing V's which wedge between the abutments and the lancet body. The cap may have a weakness leaving it rigid enough for the initial priming but which causes it to buckle if used to try to overcome the ratchet.

8 Claims, 3 Drawing Sheets

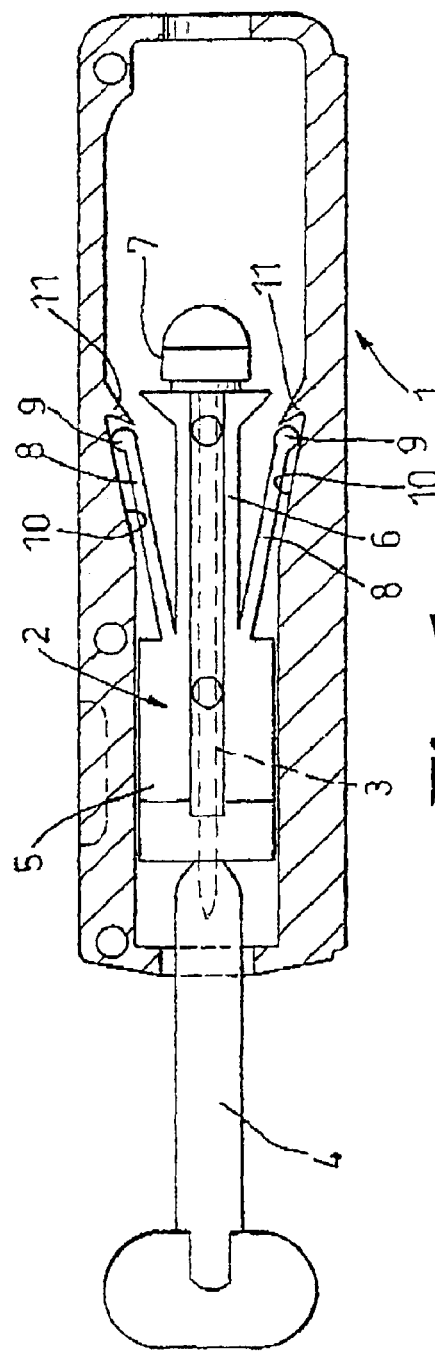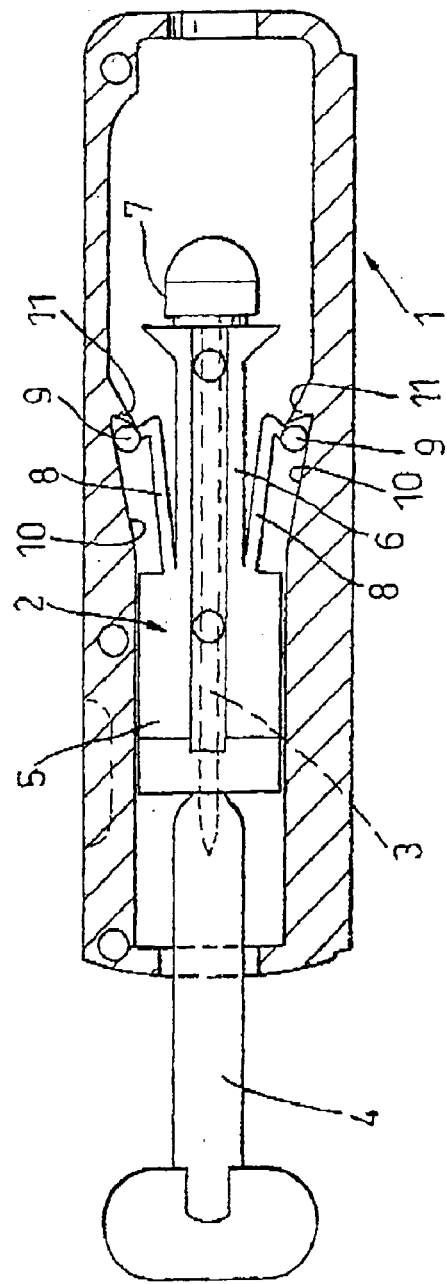

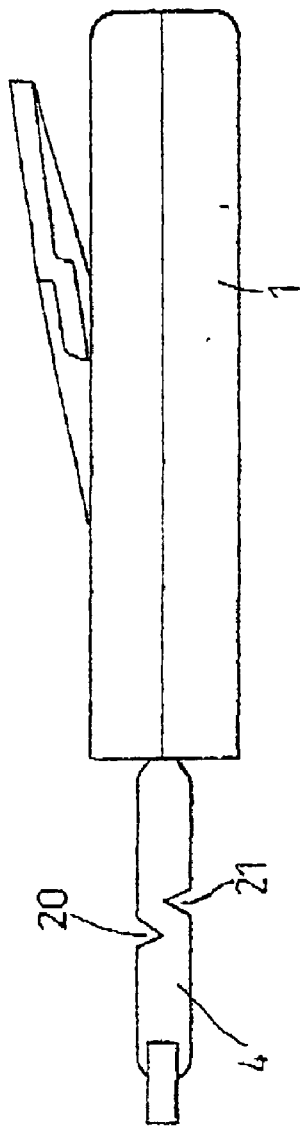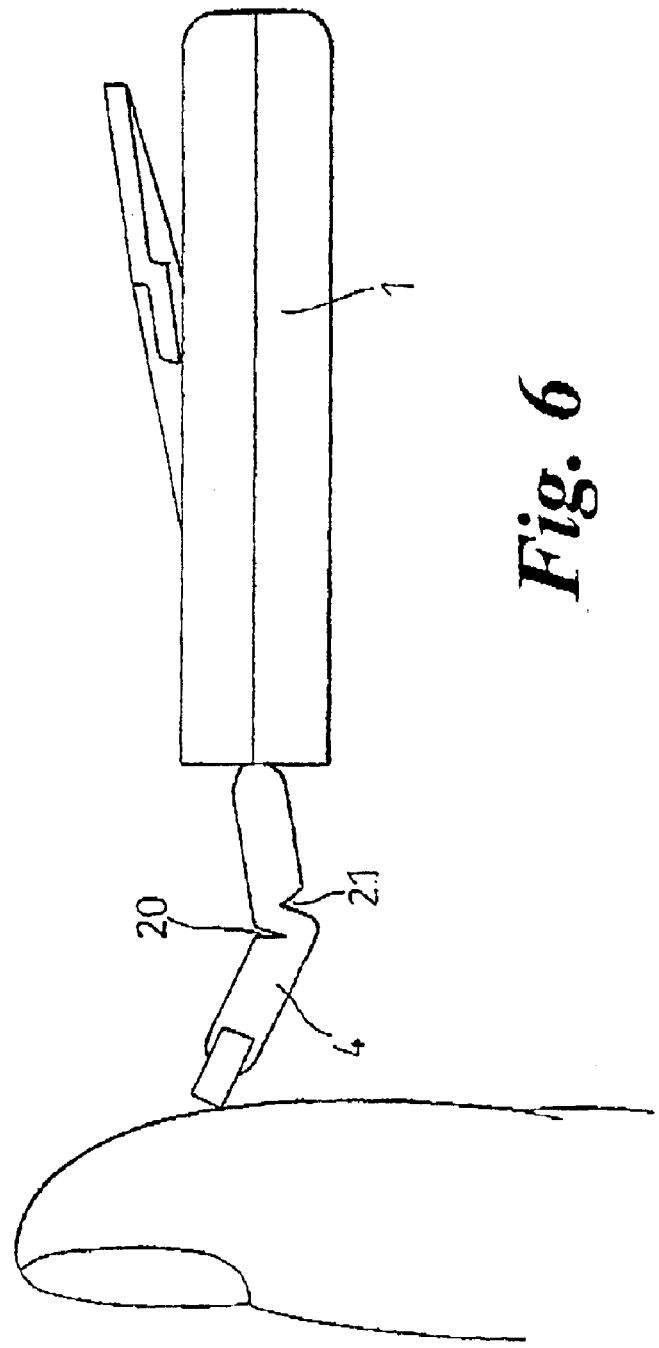
*Fig. 5*
*Fig. 6*

SKIN PRICKERS

CROSS REFERENCE TO RELATED APPLICATION

This is the 35 USC 371 national stage of international application PCT/GB01/05181 filed on Nov. 26, 2001, which designated the United States of America.

FIELD OF THE INVENTION

This invention relates to skin prickers. It is a development of that described in EP-B-0634000, and is concerned with ensuring that the lancet, once fired, cannot be pushed back via the needle tip aperture, re-cocked and re-fired.

SUMMARY OF THE INVENTION

According to one aspect of the present invention there is provided a disposable pricker comprising an elongate housing with a spring-loaded, longitudinally movable lancet carried therein, the lancet tip normally being within the housing, a trigger mechanism to retain the lancet in a fully retracted position energising the spring means and actuable to release or fire the lancet to cause the tip to have a momentary position projecting from the forward end of the housing, and means for preventing repeated use including a spring finger extending rearwardly from the lancet alongside but spaced from the body thereof, and an abutment on the inside of the housing past which the tip of the finger can snap during forward motion of the lancet, any attempt to push the lancet back with a greater than predetermined force after firing causing the finger, with its tip arrested by the abutment, to buckle into a rearward pointing V that wedges between the abutment and the body of the lancet.

Preferably, the lancet is symmetrical, with two fingers on opposite sides thereof. The housing will then have two opposed abutments, and these may be shaped as barbs pointing inwards and forwards.

In one form the or each finger inclines outwardly from the lancet body as well as extending rearwardly.

Alternatively the or each finger may be generally parallel to and spaced from the adjacent part of the body of the lancet but with its tip flaring outwardly.

The needle tip may initially be protected by an elongate cap by which the lancet can be pushed back to the fully retracted position from an initial pre-fired position with the or each finger tip immediately to the rear of the associated abutment. For preventing this cap being usable to force the lancet back beyond the position at which it is held by the abutment(s) after firing, the elongate cap preferably has a weakness that is not significant when the cap is used for retracting the lancet from said initial position. However, it will cause the cap to deform if the cap is subjected to excessive axial compression, as when being used to try to push the lancet back after firing. This weakness is conveniently achieved by way of a local reduction of the cross-section of the elongate cap, the deformation being buckling.

This cap with a weakness need not be confined to the lancet and pricker defined above.

Therefore, according to another aspect of the present invention there is provided a lancet for a skin pricker, the lancet having a plastics body integrally moulded with a breakaway cap around a needle, the cap having an elongate stem aligned with the needle and with an end encasing he needle tip, the latter being exposed when the cap is removed, wherein the stem has a zone of weakness whereby longitudinal compression of the cap above a predetermined level will cause the stem to buckle.

The zone of weakness is conveniently created by at least one notch indented into the stem, and preferably there will be two notches on opposite sides and mutually offset longitudinally of the stem. Other possibilities are a transverse bore through the stem, or the latter being formed with a neck.

BRIEF DESCRIPTION OF THE DRAWINGS

For a better understanding of the invention, some embodiments will now be described, by way of example, with reference to the accompanying drawings, in which:

FIG. 1 is an axial section of a skin pricker after its lancet has been fired,

FIG. 2 is a similar section showing an attempt to retract the lancet after firing, FIG. 5 is a side view of a skin pricker with a safety cap for the needle tip, and FIG. 6 is a similar side view showing the cap being used to try to retract a fired lancet.

DETAILED DESCRIPTION OF THE INVENTION

Figure 3:
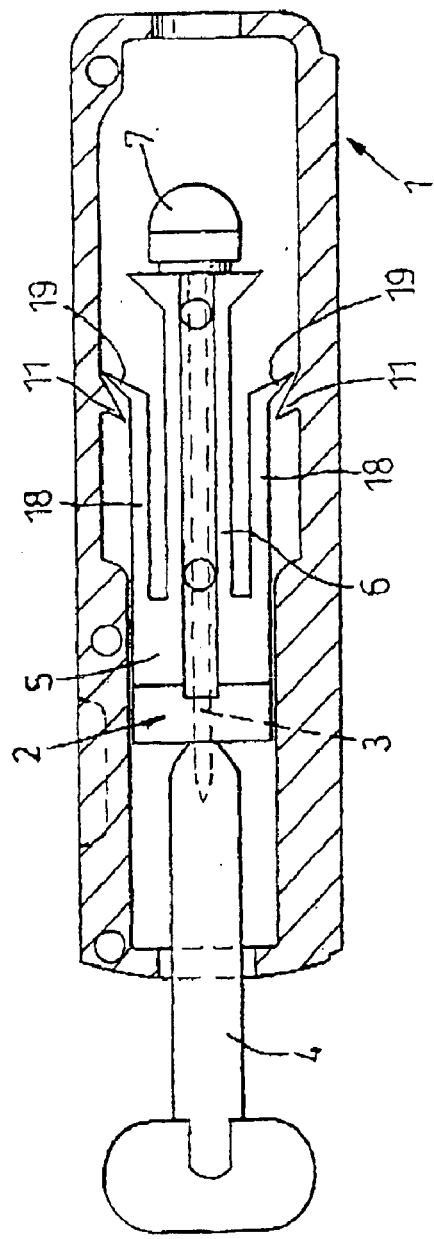
FIG. 3 is an axial section of another skin pricker before its lancet is fired.

The device of FIGS. 1 and 2 has a barrel 1 of two halves joined at a longitudinal split to hold a lancet 2. The lancet has plastics body encasing a needle 3 whose tip is initially embedded in a twist-off elongate cap 4 moulded integrally with the body. The cap serves the same purpose as that in EP-B-0634000. The spring that drives the lancet forwards and the trigger that releases it are not shown for simplicity.

The lancet body has a large head 5 non-rotatably guided in the forward part of the barrel. A stem 6 extends rearwardly from the head terminating in a formation 7 that locates the leading end of the spring. At opposite sides of the stem fingers 8 lead outwardly and rearwardly from the roots of the shoulders at the transition between the head 5 and the stem 6. They terminate in enlargements 9. Being integrally moulded with the plastics body, they are resiliently flexible and can act as springs.

At about its mid-length the interior of the barrel 1 widens towards the rear at opposite sides in gradual slopes 10 terminating in inwardly and forwardly angled barbs 11.

Initially, with the spring relaxed, the enlargements 9 are behind the barbs 11. The cap 4 is pressed to retract the lancet, and the device is then cocked. The cap is twisted off and the device is applied and fired. The thrust of the spring urges the lancet forwards and the fingers 8 flex inwards as the enlargements 9 snap past the barbs 11, just before the needle tip momentarily emerges from the forward end of the barrel. As the overextended spring retracts, the enlargements 9 slide along the slopes 10 until they engage the hooks formed by the barbs 11. There is effectively a ratchet mechanism.

This is the position shown in FIG. 1, with the cap 4 pushed back in with a view to restoring the device to its cocked condition.

However, if the cap is pushed further, while the main body of the lancet will move, at least initially, the fingers 8 are trapped. They will then buckle as shown in FIG. 2 to form rearward pointing Vs, and thus wedges that will jam between the barbs 11 and the stem 6. The enlargements 9 ensure that the ends of the fingers 8 do not flip clear of the barbs.

Thus the lancet is arrested and immobilised before the cocked position is reached, and re-firing is prevented.

Figure 4:
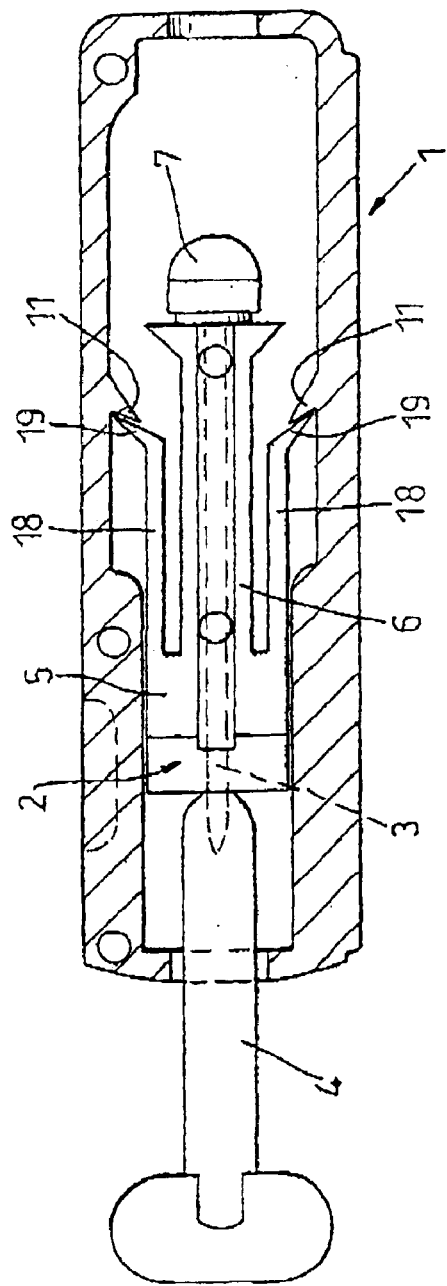
FIG. 4 is a similar section showing the lancet of FIG. 3 after firing.

The device of FIGS. 3 and 4 is similar in many respects to that of FIGS. 1 and 2, and corresponding parts are similarly referenced.

The significant difference lies in the spring fingers, now referenced 18. They extend rearwardly from the tips of the shoulders at the transition between the head 5 and the stem 6, and they normally lie parallel to and spaced from that stem. They terminate in outwardly flared tips 19.

The ratchet operation is similar to that described. When the lancet is fired, towards the end of its forward movement the tips 19 snap past the barbs 11, momentarily flexing the arms 18 inwards. The bounce back of the lancet leaves the tips 19 loosely engaging those barbs. Any rearward force on the lancet enhances that engagement, and rearward movement of the lancet is resisted by the arms 18, which remain straight under light longitudinal compression. However, once the rearward force reaches a certain level they begin to bend and the arms flex inwards rather than outwards, as shown in broken lines in FIG. 4, by virtue of the engagement of the tips by the barbs outside the main length of the arms. The tips 19 will spear outwardly as well as rearwardly into the acute angles of the barbs 11 and will therefore be less likely to jump those barbs Further force will cause the arms to buckle and wedge as in the previous embodiment.

These are necessarily small devices and the size of the barbs 11 and the arms that engage them are correspondingly small. While they will operate as described when moderate rearward force is applied to the lancet after firing, a really determined push could break down the engagement at the barbs 11 and re-cock the device. The obvious instrument for applying this push is the elongate cap 4, removed but perhaps not discarded immediately prior to use.

As a further safety measure, applicable not just to the embodiments described, the cap 4 may be constructed to render it useless for retracting the lancet after firing. In the example of FIGS. 5 and 6 two notches 20 and 21 are formed in opposite sides at slightly different axial positions around the mid-length of the stem of the cap, making a zig-zag. The cap 4 will be rigid enough for the initial cocking of the device against the spring, but if the lancet is held by the barbs 11, the cap will buckle as shown in FIG. 6 before the barbs 11 or the tips of the arms 8 or 18 give way.

Another way of weakening the cap, which may be preferred, is simply to have a transverse bore through it at around the mid-length. Alternatively, just one notch may suffice, or it may be formed with a neck.

In the embodiments described, the lancet is symmetrical, with spring arms 8 or 18 on opposite sides. While this is preferred, it would be possible to construct and guide the lancet so that only one arm would suffice.

What is claimed is:

1. A disposable pricker comprising:
    an elongate housing with a spring-loaded, longitudinally movable lancet having a body and a needle tip carried therein, the needle tip normally being within the housing;
    a trigger mechanism to retain the lancet in a fully retracted position energizing the spring loading and actuable to release or fire the lancet to cause the needle tip to have a momentary position projecting from a forward end of the housing;
    means for preventing repeated use including a spring finger having a tip and extending rearwardly from the lancet alongside but spaced from the body thereof; and
    an abutment on the inside of the housing past which the tip of the finger can snap during forward motion of the lancet, any attempt to push the lancet back with a greater than predetermined force after firing causing the finger, with the finger tip arrested by the abutment to buckle into a rearward pointing V that wedges between the abutment and the body of the lancet.

2. The disposable pricker according to claim 1, wherein the lancet is symmetrical, with two fingers on opposite sides thereof, and the housing has two opposed abutments.

3. The disposable pricker according to claim 1, wherein the abutment is shaped as a barb, pointing inwardly of and towards the forward end of the housing.

4. The disposable pricker according to claim 1, wherein the finger inclines outwardly from the lancet body and also extends rearwardly.

5. The disposable pricker according to claim 1, wherein the finger is generally parallel to and spaced from an adjacent part of the body of the lancet but with the finger tip flaring outwardly.

6. The disposable pricker according to claim 1, wherein the needle tip is initially protected by an elongate cap by which the lancet is adapted to be pushed back to the fully retracted position from an initial pre-fired position in which latter position, the finger tip is immediately to the rear of the associated abutment.

7. The disposable pricker according to claim 6, wherein the elongate cap has a weakness that is not significant when the cap is used for retracting the lancet from said initial position, but which causes the cap to deform if used to try to push the lancet back after firing.

8. The disposable pricker according to claim 7, wherein the weakness is by way of a local reduction of the cross-section of the elongate cap, the deformation being buckling.

* * * * *